United States Patent [19]

Lentz et al.

[11] Patent Number: 4,620,055
[45] Date of Patent: Oct. 28, 1986

[54] PREPARATION OF STYRENE AND STILBENE COMPOUNDS

[75] Inventors: Carl M. Lentz, Mt. Carmel; James R. Overton; David D. Cornell, both of Kingsport, all of Tenn.

[73] Assignee: Eastman Kodak Company, Rochester, N.Y.

[21] Appl. No.: 785,031

[22] Filed: Oct. 7, 1985

Related U.S. Application Data

[63] Continuation of Ser. No. 643,323, Aug. 22, 1984, abandoned.

[51] Int. Cl.$^4$ .................................................. C07C 15/40
[52] U.S. Cl. ................................ 585/438; 546/352; 548/560; 549/80; 585/435
[58] Field of Search .................... 585/435, 438, 446

[56] References Cited

U.S. PATENT DOCUMENTS 3,855,329 12/1974 Shue ..................................... 585/438

OTHER PUBLICATIONS

Chem Abst, 89, 41911(d), 1978.
Chem Abst, 99, 157527(u), 1983.
Chem Abst, 101, 72368(c), 1984.

*Primary Examiner*—Christopher A. Henderson
*Attorney, Agent, or Firm*—Clyde L. Tootle; David E. Cotey; J. Frederick Thomsen

[57] ABSTRACT

The present invention provides a novel process for the preparation of styrene, stilbene, and/or substituted derivatives thereof. The process involves the reaction of an aryl sulfonyl chloride with an olefinic compound in the presence of a catalytic amount of a metal catalyst consisting essentially of palladium.

9 Claims, No Drawings

PREPARATION OF STYRENE AND STILBENE COMPOUNDS

This is a continuation of application Ser. No. 643,323 filed Aug. 22, 1984.

BACKGROUND OF THE INVENTION

The present invention relates to a novel process for the preparation of styrene, stilbene, and substituted derivatives thereof. The process comprises reacting an aryl sulfonyl chloride with an olefinic compound in the presence of a specified catalyst.

In typical prior art processes for the preparation of styrene, ethylbenzene is dehydrogenated to form the desired product. It is further known in the art that stilbene can be produced by the partial oxidation of toluene in the presence of a catalyst. For example, in one such process, toluene is passed over hot lead oxide so as to yield stilbene.

In contrast to the prior art processes described above, the present invention provides a flexible process which can be used for the preparation of a relatively broad class of compounds including styrene, stilbene, and substituted derivatives thereof.

SUMMARY OF THE INVENTION

The present invention relates to a process for the preparation of compounds of the formula Ar-CH=CH-R, wherein Ar represents a carbocyclic or heterocyclic aromatic moiety having about 5 to 20 atoms in the ring or rings thereof, and R represents H, an alkyl group having up to about 12 carbon atoms, or a substituted or unsubstituted phenyl group. The process of the present invention comprises reacting an aryl sulfonyl chloride of the formula ArSO$_2$Cl, wherein Ar is as defined above, with an olefinic compound of the formula

R-CH=CH$_2$, wherein R is as defined above, in the presence of a catalyst consisting essentially of palladium.

DETAILED DESCRIPTION OF THE INVENTION

The present invention relates to the production of styrene, stilbene, or substituted derivatives thereof by a process which involves the catalytic reaction of an olefinic compound with an aryl sulfonyl chloride in the presence of a catalyst consisting essentially of palladium.

The aryl sulfonyl chloride employed as a starting material in the process of the present invention has the following chemical formula:

ArSO$_2$Cl

In the above formula, Ar represents a carbocyclic or heterocyclic aromatic moiety having about 5 to about 20 atoms in the ring or rings thereof. Such moieties can be derived from, for example, toluene, benzene, naphthalene, pyridine, thiophene, pyrrole, etc.

The aromatic moiety of the aryl sulfonyl chloride can be substituted or unsubstituted. When substituted, typical substituents include the halides, alkyl groups having up to about 12 carbon atoms, vinyl, carboxylic acid moieties, carboxylic ester moieties, ether groups, nitro groups, etc.

Thus, examples of the aryl sulfonyl chloride include benzenesulfonyl chloride, p-toluenesulfonyl chloride, p-nitrobenzenesulfonyl chloride, p-methoxybenzenesulfonyl chloride, p-isopropylbenzenesulfonyl chloride, p-2-ethylhexylbenzenesulfonyl chloride, etc.

The preparation of aryl sulfonyl chlorides is well known in the art. See, for example, *Organic Chemistry* by R. T. Morrison and R. N. Boyd (Second Edition), pp. 706-07, the teachings of which are incorporated herein by reference.

In accordance with the process of the present invention, an aryl sulfonyl chloride, as described above, is reacted with an olefinic compound of the formula R-CH=CH$_2$. In the above formula, R represents H, an alkyl group having up to about 12 carbon atoms, or a substituted or unsubstituted phenyl group. In the case where R represents a substituted phenyl group, typical substituents include the halides, alkyl groups having up to about 12 carbon atoms, vinyl, carboxylic acid moieties, carboxylic ester moieties, ether groups, nitro groups, etc. Thus, examples of the olefinic compound include ethylene, propylene, styrene, p-methylstyrene, ethenylbenzoic acid and lower alkyl esters thereof, etc.

The reaction system of the present process further comprises a metal catalyst. The catalyst consists essentially of palladium. The active metal species appears to be the zero-valent form of the metal. Therefore, in preferred embodiments, the catalyst is provided to the reaction system in the zero-valent form of the metal. More preferably, the zero-valent The catalyst metal may also be provided in a higher valence state, provided that an in situ reduction to the zero-valent form occurs. Thus, palladium salts, such as palladium acetate, palladium chloride, etc., are also suitable catalyst materials.

The catalyst is present in a concentration of at least about 0.1 mole percent, based on the concentration of the aryl sulfonyl chloride (preferably, about 0.1 to 10 mole percent).

The process of the present invention can be conducted at room temperature or at elevated temperatures up to about 150° C. Preferably, the temperature of the reaction is in the range of about 25° to 75° C.

In preferred embodiments, the process of the present invention is conducted at atmospheric pressure. However, if volatile reactants are employed, it may be desirable to employ superatmospheric pressures (e.g., up to about 100 atmospheres).

It may be desirable also to include in the reaction system a base having a pK$_a$ greater than that of pyridine. The presence of such a base may aid in the prevention of deactivation of the metal catalyst. When employed, the base is present in an amount of about 1 to 10 equivalents of base per equivalent of sulfonyl chloride. Preferably, about 3 equivalents of base per equivalent of sulfonyl chloride is employed. Preferred bases include trialkylamines (such as triethylamine), sodium carbonate, potassium carbonate, etc.

Inert solvents may be employed, but are not necessary. Such solvents may include, for example, tetrahydrofuran, acetonitrile, methylene chloride, diethyl ether, etc.

While not wishing to be bound by theoretical considerations, it is believed that the process of the present invention involves the following reaction pathway:

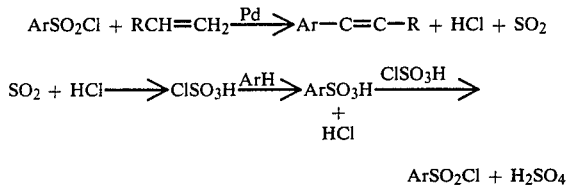

In the above-described reaction scheme, the $SO_2$ and HCl by-products can be removed from the reaction system and then employed in the preparation of the sulfonyl chloride starting material. For example, as shown, the $SO_2$ and HCl by-products can be reacted together to form chlorosulfonic acid, which can then be reacted in excess with the aryl compound so as to form the sulfonyl chloride. Alternatively, the $SO_2$ can be reacted with water to produce sulfuric acid, which can then be reacted with the aryl compound to form the corresponding sulfonic acid. The sulfonic acid can be reacted by known processes (for example, with phosphorus pentachloride or thionyl chloride) so as to produce the desired sulfonyl chloride which is employed as starting material in the present process.

The present invention provides a flexible process which is capable of producing a wide range of ethylenically unsaturated aromatic compounds. These compounds include styrene, stilbene, and substituted derivatives thereof. These compounds have well known uses as monomers (e.g., as precursors for liquid crystalline polyesters), as dye intermediates, etc.

The invention will be further illustrated by the following Examples although it will be understood that these Examples are included merely for purposes of illustration and are not intended to limit the scope of the invention.

EXAMPLE 1

This Example illustrates the preparation of t-4,4'-dimethylstilbene by the reaction of p-toluenesulfonyl chloride with p-methylstyrene.

A 100 ml 3-neck, round-bottom flask was fitted with a reflux condenser, magnetic stirrer, and thermometer. To the described apparatus were added 0.95 g (5 millimoles) of p-toluenesulfonyl chloride, 0.5 g (5 millimoles) of p-methylsytyrene, 0.11 g (0.5 millimoles) of palladium acetate, 0.5 g (5 millimoles) of triethylamine, and 40 ml of tetrahydrofuran. The mixture was heated to reflux and held at reflux for four hours. After cooling to 25° C., the mixture was filtered through a Celite ® pad in order to remove Pd in its zero-valent state as a black powder. Water (200 ml) was added to the filtrate to solubilize any $SO_2$, HCl, and/or $Et_3N$ present in the system. The resulting solution was extracted with 2×100 ml of diethyl ether. The product, which is insoluble in water, was thereby extracted from the aqueous mixture into the ether layer. The ether extracts were combined and washed with 100 ml of 10% HCl. The ether extracts were dried over magnesium sulfate and the solvent was removed in vacuo to afford a golden colored solid. The solid was dissolved in hexane containing 10% methylene chloride and was subjected to chromatography on 100 g of silica gel. The product was eluted with 500 ml of hexane. The solvent was removed and 0.82 g (81%) of a white solid was obtained. The product was identical in all respects to authentic t-4,4'-dimethylstilbene.

The invention has been described in detail with particular reference to preferred embodiments thereof, but it will be understood that variations and modifications can be effected within the spirit and scope of the invention.

We claim:

1. A process for the preparation of styrene and stilbene compounds which comprises reacting at a temperature of about 25° to 150° C. and a pressure of about 1 to 100 atmospheres an aryl sulfonyl chloride of the formula $ArSO_2Cl$, wherein Ar represents a moiety derived from benzene or toluene, with an olefinic compound of the formula $R-CH=CH_2$, wherein R represents H, an alkyl group having up to about 12 carbon atoms, or a substituted or unsubstituted phenyl group, in the presence of a base having a pKa greater than that of pyridine and a catalyst consisting essentially of palladium in a concentration of about 0.1 to 10 mole percent based on the concentration of said aryl sulfonyl chloride.

2. The process of claim 1 wherein the reaction temperature is about 50° to 100° C.

3. The process of claim 1 wherein said base comprises triethylamine, sodium carbonate, or potassium carbonate.

4. The process of claim 1 wherein the reaction system further comprises an inert solvent.

5. The process of claim 4 wherein said inert solvent comprises tetrahydrofuran, acetonitrile, methylene chloride, or diethyl ether.

6. The process of claim 5 wherein said Ar represents toluene.

7. The process of claim 6 wherien said aryl sulfonyl chloride is p-toluenesulfonyl chloride.

8. The process of claim 7 wherein said compounds of the formula $Ar-Ch=CH-R$ is 4,4'-dimethylstilbene.

9. A process for the preparation of styrene compounds which comprises reacting at a temperature of about 25° to 150° C. and a pressure of about 1 to 100 atmospheres an aryl sulfonyl chloride of the formula $ArSO_2Cl$, wherein Ar represents a moiety derived from benzene, with an olefinic compound of the formula $R-CH=CH_2$, wherein R represents H, an alkyl group having up to about 12 carbon atoms, or a substituted or unsubstituted phenyl group, in the presence of a base having a pKa greater than the of pyridine and a catalyst consisting essentially of palladium in a concentration of about 0.1 to 10 mole percent, based on the concentration of said aryl sulfonyl chloride.

* * * * *